United States Patent [19]

Audia

[11] Patent Number: 5,064,850

[45] Date of Patent: Nov. 12, 1991

[54] DIHYDRO-3,3-DIPHENYL-5-(1H-PYRAZOL-1-YLMETHYL-2(3H)-FURANONE AND DIHYDRO-5-((SUBSTITUTED-1H-PYRAZOL-1-YL)METHYL)-3,3-DIPHENYL-2(3H)-FURANONE DERIVATIVES

[75] Inventor: Vicki H. Audia, Finksburg, Md.

[73] Assignee: Marion Merrell Dow Inc., Kansas City, Mo.

[21] Appl. No.: 681,761

[22] Filed: Apr. 8, 1991

[51] Int. Cl.$^5$ .................. A61K 31/415; C07D 405/06
[52] U.S. Cl. ..................................... 514/406; 548/374
[58] Field of Search ........................ 548/374; 514/406

[56] References Cited
FOREIGN PATENT DOCUMENTS
42-108  1/1967  Japan .

*Primary Examiner*—Robert W. Ramsuer
*Attorney, Agent, or Firm*—Theresa M. Gillis

[57] ABSTRACT

Dihydrofuranone compounds having anticholinergic activity are described. The compounds have the formula:

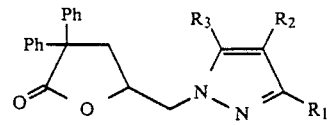

wherein:
$R_1$ is hydrogen or lower alkyl,
$R_2$ is hydrogen or lower alkyl,
$R_3$ is hydrogen or lower alkyl, and
Ph is phenyl.

Also described are the lower alkyl quaternary and acid addition salts of the compounds. Pharmaceutical compositions effective as anticholinergics and methods utilizing such compounds are disclosed.

24 Claims, No Drawings

DIHYDRO-3,3-DIPHENYL-5-(1H-PYRAZOL-1-YLMETHYL-2(3H)-FURANONE AND DIHYDRO-5-((SUBSTITUTED-1H-PYRAZOL-1-YL)METHYL)-3,3-DIPHENYL-2(3H)-FURANONE DERIVATIVES

BACKGROUND OF THE INVENTION

1. Field of the Invention

This invention relates to novel dihydro-3,3-diphenyl-5-(1H-pyrazol-1-ylmethyl)-2(3H)-furanone and dihydro-5-[(substituted-1H-pyrazol-1-yl)methyl]-3,3-diphenyl-2(3H)-furanone derivatives, and their pharmaceutically acceptable lower alkyl quaternary and acid addition salts. The compounds have anticholinergic activity.

2. State of the Art

Antagonism of the action of acetylcholine at muscarinic cholinergic receptors in various tissues produces antispasmodic, antisecretory and mydriatic effects. As a result, such compounds have a broad range of therapeutic applications, notably as antispasmodics, as an adjunct in the treatment of peptic ulcer, as adjuvants in the treatment of functional disorders of the bowel or bladder, such as irritable bowel syndrome, spastic colitis, ulcerative colitis, diverticulitis and neurogenic bladder disorders (B.V. Rama Sastry in "Burger's Medicinal Chemistry", M. E. Wolff, Ed., 4th Ed., Part III, chap. 44, pg. 361).

Furanones have long been known in the realm of natural products chemistry. Pilocarpine, a 4-[1-(imidazol)methyl] 2(3H)furanone, is a naturally occurring muscarinic agonist (L. S. Goodman, A. Gilman, "The Pharmacological Basis of Therapeutics", 6th Ed., 1980, p. 87). 5-[(Diethylamino)methyl]-4,5-dihydro-3,3-diphenyl-2(3H)furanone is a furanone for which antiarrhythmic effectiveness in mammalian heart tissue, but not anticholinergic properties, has been described (A. Poland, S. African Patent 68 05, 631, Mar. 2, 1970, Eli Lilly and Co., U.S. applied Nov. 13, 1967). Another furanone, a spasmolytic that prevents contractions of isolated guinea pig ileum, is 3-[(dimethylamino)methyl]-4,5-dihydro-5,5-diphenyl-2(3H)furanone (N. Kolokouris, G. Fytas, C. Brunet, M. Luyckx, *Ann. Pharm. Fr.* 43(3), 1985. p. 257. The majority of presently known antimuscarinic agents are structurally similar to solanaceous alkaloids, e.g., atropine, or a diverse group of compounds including hydroxyesters, e.g., oxybutynin, amides, e.g., tropincamide, and amino alcohols, e.g., procyclidine. These groups of compounds block the effect of acetylcholine on the cholinergic receptor. The isopropyl quaternary bromide of atropine, i.e. ipratropium bromide, is particularly noteworthy for its use as a bronchodilator in the treatment of respiratory disorders, such as asthma and chronic bronchitis (G. E. Pakes, R. N. Brogden, R. C. Heel, T. M. Speight, G. S. Avery, *Drugs.* 20, 1980, 237–266.

The present invention provides a novel class of dihydro-3,3-diphenyl-5-(1H-pyrazol-1-ylmethyl)-2(3H)-furanone and dihydro-5-[(substituted-1H-pyrazol-1-yl)methyl]-3,3-diphenyl-2(3H)-furanone derivatives which have anticholinergic activity

SUMMARY OF THE INVENTION

The invention provides novel compounds of Formula I:

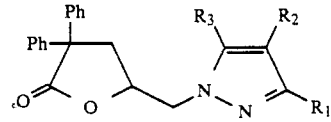

in which:
 $R_1$ is hydrogen or lower alkyl,
 $R_2$ is hydrogen or lower alkyl,
 $R_3$ is hydrogen or lower alkyl, and
 Ph is phenyl
and the pharmaceutically acceptable lower alkyl quaternary and acid addition salts thereof.

As used herein, lower alkyl refers to groups having one to three carbons. Each R group may be different than the other groups, i.e., each R group is independently selected.

The invention also includes pharmaceutical compositions effective as anticholinergics and therapeutic methods utilizing such compounds in those disorders in which anticholinergic agents are recognized to be effective.

DETAILED DESCRIPTION OF THE INVENTION

This invention is directed to dihydro-3,3-diphenyl-5-(1H-pyrazol-1-ylmethyl)-2(3H)-furanone and dihydro-5-[(substituted-1H-pyrazol-1-yl)methyl]-3,3-diphenyl-2(3H)-furanone derivatives of Formula I set forth above. Preferred compounds are those in which $R_1$, $R_2$ and $R_3$ are each independently hydrogen or methyl. More preferred compounds are those in which $R_3$ is hydrogen and $R_2$ and $R_1$ are hydrogen or methyl. The most preferred $R_1$ and $R_2$ groups are hydrogen. Among the preferred compounds are dihydro-3,3-diphenyl-5-(1H-pyrazol-1-ylmethyl)-2(3H)-furanone, dihydro-5-[3-methyl-1H-pyrazol-1-ylmethyl]-3,3-diphenyl-2(3H) furanone, methyl dihydro-3,3-diphenyl-5-(1H-pyrazol-1-ylmethyl)-2(3H)-furanone, ethyl dihydro-3,3-diphenyl-5-(1H-pyrazol-1-ylmethyl)-2(3H)-furanone, ethyl dihydro-5-](3-methyl-1H-pyrazol-1-yl)methyl]-3,3-diphenyl-2(3H)-furanone, and methyl dihydro-5-[(3-methyl-1H-pyrazol-1-yl)methyl ]-3,3-diphenyl-2(3H)-furanone.

To the extent the compounds of the invention may exist as optical or geometric isomers, all isomers and racemic mixtures are understood to be included in the invention. In addition, all possible other isomeric forms of the compounds of the invention are within the ambit of this invention.

The invention includes the nontoxic, pharmaceutically acceptable salts of the compounds of Formula I. Among the salts which may be used are the lower alkyl quaternary halide and acid addition salts of the compounds. Such salts may be prepared by methods well known to the art. The acid addition salts may be formed with both inorganic or organic acids, for example: Maleic, fumaric, benzoic, ascorbic, pamoic, succinic, bis-methylenesalicyclic, methane sulfonic, ethanedisulfonic, acetic, oxalic, propionic, tartaric, salicylic, citric, gluconic, lactic, mandelic, cinnamic, citraconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. The lower alkyl quaternary halide salts are preferably formed from methyl or ethyl chloride.

The compounds of the invention act as cholinergic receptor antagonists. They may be administered to patients in whom promotion of anticholinergic activity is desirable. They have a variety of antimuscarinic therapeutic applications, particularly in the treatment of neurogenic bladder. As a result of their action on the bladder, and their antispasmodic and antisecretory effects, they are of particular benefit in the treatment of urinary incontinence. The compounds also can be expected to produce antispasmodic, antisecretory and mydriatic effects useful in other disorders, notably as antispasmodics, as an adjunct in the treatment of peptic ulcer, and as adjuvants in the treatment of functional disorders of the bowel or bladder, such as irritable bowel syndrome, spastic colitis, ulcerative colitis and diverticulitis. The free base furanones are suprisingly potent at the muscarinic receptors of ileum preparations ($M_3$), yet selective for the $M_3$ receptor over the $M_2$ receptor found in atrial preparations. The quaternary salts of this invention are potent at the $M_3$ receptor as measured in ileal preparations.

The compounds of this invention may be administered orally, parenterally, or by inhalation in conventional dosage unit forms such as tablets, capsules, injectables, aerosols, or the like, by incorporating the appropriate dose of a compound of Formula I with carriers according to accepted pharmaceutical practices.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent can include any time delay material well known to the art, such as glycerol monostearate or glycerol distearate alone or with a wax.

A wide variety of pharmaceutical forms can be employed. If a solid carrier is used, the preparation can be tableted, placed in a hard gelatin capsule in powder or pellet form, or in the form of a troche or lozenge. The amount of solid carrier will vary widely, but preferably will be about 25 mg to about 1 g. If a liquid carrier is used, the preparation will be in the form of a syrup, emulsion, soft gelatin capsule, aerosol, sterile injectable liquid such as an ampoule, or an aqueous or nonaqueous liquid suspension.

Preferably, a compound, a lower alkyl quaternary salt thereof, or an acid addition salt thereof is administered orally to an animal organism in a tablet, capsule or aerosol containing an amount sufficient to produce the desired activity of a cholinergic antagonist. Generally, each dosage unit will contain the active ingredient in an amount of about 0.1 mg to about 40 mg. Advantageously equal doses will be administered three to four times daily with the daily dosage regimen being about 1 mg to about 160 mg, preferably from about 6 mg to about 80 mg.

The compounds of the invention can be prepared by alkylation of diphenylacetic acid. For example, diphenylacetic acid was dilithiated and treated with allyl bromide to yield 2,2-diphenyl-4-pentenoic acid. This acid was cyclized to the furanone by treatment of the 2,2-diphenyl-4-pentenoic acid in formic acid with hydrogen peroxide followed by treatment with sodium hydroxide in aqueous methanol. Acidification provided the furanone which was allowed to react with trifluoromethane sulfonic anhydride in dichloromethane to afford the 5-[1-(trifluoromethanesulfonyl)methyl]-3,3-diphenyl-2- furanone. This triflate derivative was employed for alkylation of the appropriate pyrazole to produce a dihydro-3,3-diphenyl-5-(1H-pyrazol-1-ylmethyl)-2(3H)-furanone derivative or dihydro-5-[(substituted-1H-pyrazol-1-yl)methyl]-3,3-diphenyl-2(3H)-furanone derivatives.

Stereoselective syntheses of compounds of this invention proceeded from (R) and (S)-2,2-dimethyl-4-(hydroxymethyl)-1,3-dioxolane via the corresponding 4-iodomethyl derivative with which a phenylacetic acid was alkylated. Hydrolysis of the dioxolane afforded a diol, which following lactonization to the corresponding 5-hydroxymethyl-4,5-dihydro-3,3-disubstituted-2(3H) furanone, was converted to the 5-[1-(trifluoro methanesulfonyl)methyl]-3,3-diphenyl-2-furanone and then used to alkylate pyrazole as indicated in the preceeding paragraph.

The following examples are illustrative of the invention. Temperature is expressed in degrees Celsius; NMR signals are given as ppm downfield from an internal standard of $Me_4Si$.

EXAMPLES

Example 1

(a) 5-Hydroxymethyl-3,3-diphenyl-2(3H)-furanone. To a mixture of 49.5 g (0.196 mol) of diphenylpenten-1-oic acid in 203.4 mL (5.39 mol) of formic acid was added 22.4 mL (0.22 mol) of 30% hydrogen peroxide. The mixture was heated to 90° C. then cooled to 70° C. over 30 min and stirred for 30 min. The mixture was cooled and the solvent was removed from the gray-green mixture at reduced pressure. The residue was diluted with 200 mL of methanol followed by 125 mL of water. To the aqueous methanolic mixture was added 30.8 g (0.77 mol) of sodium hydroxide. The mixture was heated to 70° C. with stirring for 1 h then cooled and stirred overnight. The mixture was cooled to 5°-0° C. and 6N HCl was added until mixture was acidic. Mixture was extracted with ether (6×200 ML) and combined ether extracts were washed with water (2×500 mL) and dried over sodium sulfate. Filtration and removal of solvent gave an orange viscous oil, 51.98 g (98%). TLC (silica, 90:10 dichloromethane:ethyl acetate) $R_f$ 0.54 (lactone) $R_f$ 0.71 (side product). Crude lactone alcohol was diluted with ether and washed with saturated sodium bicarbonate (3×200 mL), dried over sodium sulfate. Filtration and concentration gave 39.24 g of a sticky orange solid. 1H NMR (CDCl3) 2.1 8 (br s, 1H), 2.87-2.97(m, 2H), 3.69 (dd, J=4.5Hz,)=12.6Hz, 1H), 4.5-4.42 (m, 1H), 3.98 (dd, J=2.7 Hz, J=12.6 Hz, 1H), 7.23-7.37 (m).

(b) 5-[1-(trifluoromethanesulfonyl)methyl]-3,3-diphenyl-2-furanone. To a solution of 0.80 mL (4.77 mmol) of trifluoromethanesulfonic anhydride in 2.0 mL of dichloromethane was added 0.33 g (3.09 mmol) of sodium carbonate at −55° C. under argon. The mixture was stirred vigorously and 1.00 g (3.72 mmol) of the 5-hydroxymethyl lactone in 3.0 mL of dichloromethane was added dropwise over 12.0 min. The orange-tan mixture was stirred at −50° to −30° C. for 2.2 h then at 0° to −5° C. for 1.2 h. The mixture was quenched with addition of 3.0 mL of water then diluted with 6.0 mL of dichloromethane. Layers were separated and aqueous layer (pH 1) was extracted with dichloromethane (3×10 mL), and combined organic layers were washed with brine (3×15 mL), and dried over sodium sulfate. Filtration and removal of solvent gave a glassy tan solid, 1.37 g (92%). TLC (silica, 80:20 ethyl acetate/hexane) $R_f$ 0.46. 1H NMR (CDCl$_3$) 2.83 (dd, J=15Hz, J=12 Hz, 1H), 3.07 (dd, J=18 Hz, J=3 Hz, 1H), 4.57–4.71 (m).

(c) Dihydro-3,3-diphenyl-5-(1H-pyrazol-1-ylmethyl)-2(3H)-furanone. To a mixture of 12.00 g (29.9 mmol) of the lactone triflate in 40.0 mL of dichloromethane was added 3.12 g (44.9 mmol) of pyrazole under argon. The mixture was stirred vigorously in a 100° C. oil bath overnight. The mixture was cooled to room temperature and the solids were collected by filtration with an ether rinse.

Crystallization from ethanol afforded a tan solid that was dissolved in dichloromethane and washed with saturated sodium bicarbonate (4×100 mL), water (3×100 mL), and dried (Na$_2$SO$_4$). Filtration and removal of solvent gave an oil that was crystallized from ethanol: acetone (1:15) to afford 4 08 g (43%) of a solid, mp 141.5–142.5° C. $^1$H NMR (DMSO) 2.66 (dd, J=10.8, J=13, 1H, CH$_2$), 3.22 (dd, J=4.8, J=13, 1H, CH$_2$), 3.29(s, H$_2$O), 4.45–4.53 (m, 2H, CH$_2$), 4.55–4.67 (m, 1H, CH), 6.26 (t, 1H, CH), 7.1–7.45 (m, 10H), 7.46 (d, 1H), 7.73 (d, 1H, CH). IR (KBr) 3118, 3064, 2944, 1761, 1493, 1447, 1396, 1329, 1172 cm$^{-1}$. Anal calcd. for C$_{20}$H$_{18}$N$_2$O$_2$+0.25 H$_2$O: C, 74.40; H, 5.78; N, 8.68. Found: C, 74.52, 74.48; H, 5.57, 5.64; N, 8.51.

Example 2

Dihydro-5-[(3-methyl-1H-pyrazol-1-yl)methyl]-3,3-diphenyl-2(3H)-furanone. To a solution of 7.42 g (18.5 mmol) of the lactone triflate in 50 mL of dichloromethane produced in step b of Example 1 was added 3.31 mL (39.8 mmol) of 3-methylpyrazole. The mixture was sealed in high pressure tube and heated in oil bath at 100° C. for 42 h. The mixture was cooled to ambient temperature and stirred for several hours then diluted with dichloromethane. The dichloromethane layer was washed with saturated sodium bicarbonate (3×200 mL), water (3×150 mL), and dried (Na$_2$SO$_4$) Filtration and removal of solvent afforded a crude solid. Chromatoqraphy on 210 g of 230-400 mesh Merck silica gel gave an oil. Repeated crystallization from ethanol gave 1.11 g (18%) of a white solid, mp 112°–113° C. 1H NMR (DMSO) 2.12 (s, 3H, CH$_3$), 2.69 (dd, J=11, J=13, 1H, CH$_2$), 3.21 (dd, J=4.8, J=13, 1H, CH$_2$), 4.3–4.42 (m, 2H, CH$_2$), 4.52–4.65 (m, 1H, CH$_2$), 6.02 (d, 1H, CH), 7.06–7.38 (m, 1OH), 7.58 (d, 1H, CH). IR (KBr) 3424, 1769, 1171, 1072, 966, 763, 753, 704 cm$^{-1}$. Anal. Calcd. for C$_{21}$H$_{20}$N$_2$O$_2$: C,75.88; H, 6.06; N, 8.43. Found : C, 75.67; H, 6.12; N, 8.38.

Example 3

Dihydro-5-[(4-methyl-1H-pyrazol-1-yl)methyl]-3,3-diphenyl-2(3H)-furanone. To a solution of 7.93 g (19.8 mmol) of the lactone triflate in 20 mL of dichloromethane produced in step b of Example 1 was added 2.10 g (25.3 mmol) of 4-methylpyrazole in 5.0 mL of dichloromethane under argon. The mixture was sealed under argon in a pressure reaction vessel and stirred at ambient temperature for 24 h. The mixture was diluted with dichloromethane and washed with sodium carbonate (2×125 mL) water (2×100 mL) and dried (Na$_2$SO$_4$) Filtration and removal of solvent gave a dark oily residue. TLC (silica, 4:4:2, ether:hexane:dichloromethane) $R_f$ 0.66, 0.58, 0.46, 0.12. Flash chromatography on Merck silica gel (230–400 mesh) (200 g) with 1.8 L eluant of 4:4:2 ether:hexane:dichloromethane afforded an oil, TLC (silica, 4:4:2, ether:hexane: dichloromethane) $R_f$ 0.58. The oil was crystallized from ethanol and dried to afford 2.96 g (45%) of the product, mp 100.5°–102° C. (1H NMR (DMSO) 1.99 (s, 3H), 2.67 (dd, J=10.8 J=13, 1H), 3.24 (dd, J=4.8, J=13.5, 1H), 4.35–4.53 (m, 2H), 4.55–4.64 (m, 1H) 7.12–7.40 (m,), 7.48 (s, 1H). IR (KBr) 2936, 2921, 1781, 1494, 1447, 1429, 1362, 1165, 1087, 1018, 984, 964 cm$^{-1}$. Anal. calcd. for C$_{21}$H$_{20}$N$_2$O$_2$: C, 75.88; H, 6.06; N, 8.43. Found: C, 75.64, 75.61; H, 6.13, 6.13; N, 8.15, 8.17.

Example 4

Dihydro-5-[(3,5-dimethyl-1H-pyrazol-1-yl)methyl]-3.3-diphenyl-2(3H)-furanone hydrochloride. To a solution of 4.6 g (11.4 mmol of the lactone triflate in 15 mL of dichloromethane produced in step b of Example 1 was added 1.33 g (13.8 mmol) of 3,5-dimethylpyrazole under argon. The mixture was sealed in a pressure reaction vessel and heated in an 80° C. oil bath for 42 h. The mixture was cooled to ambient temperature then poured into water and extracted with dichloromethane (4×50 mL). The combined organics were washed with water (4×75 mL) and dried (Na$_2$SO$_4$) Filtration and removal of solvent gave an orange oily residue. TLC (silica, 4:4:2, ether:hexane: dichloromethane) $R_f$ 0.4 $R_f$ 0.27 flash chromatography on silica gel (230–400 mesh) (180 g) afforded a frothy solid, 2.71 g, TLC (silica, 95:5 CH$_2$Cl$_2$: CH$_3$OH) $R_f$ 0.8, $R_f$ 0.64. $^1$H NMR (DMSO) 2.04 (s, 3H), 2.20 (s, 3H), 2.81 (dd, J=10, J=13, 1H), 3.24 (dd, J=5.1, J=13, 1H), 4.26–4.31 (m, 2H), 4.55–4.64 (m, 1H), 5.8 (5.1H), 7.15–7.41 (m, 10H). To 2.7 g (7.8 mmol) of the 3.5-dimethylpyrazole lactone in 30 mL of acetone and 5 mL of ethanol was added 7.8 mL (7.8 mmol) of 1N hydrochloric acid in anhydrous ether. The solution was allowed to reach ambient temperature then cooled in a freezer to afford 1.36 g (46%) of a white solid, mp 176.5°–179° C. $^1$H NMR (DMSO) 2.09 (s, 3H), 2.23 (s, 3H) 2.81 (dd, J=10.5, J=13, 1H), 3.26 (dd, J=4.8, J=13, 1H), 4.35–4.39 (m,), 4.41–4.62 (m,), 5.91 (s, 1H), 7.18–7.42 (10H). IR (KBr) 2985, 3124, 2322, 1766, 1592, 1499, 1447, 1290, 1162, 1072, 962, 838, 810, 795, 699, 642 cm$^{-1}$. Anal. calcd. for C$_{22}$H$_{23}$O$_2$N$_2$Cl: C, 69.01; H, 6.05; N, 7.32; Cl, 9.26. Found: C, 69.09; H, 6.06; N, 7.30; Cl, 9.19.

Example 5

Methyl dihydro-3,3-diphenyl-5-(1H-pyrazol-1-ylmethyl)-2(3H)-furanone chloride hydrate. To a solution of 0.300 g (0.94 mmol of the pyrazole lactone in 3.0 mL of dichloromethane produced in Example 1 was added dropwise 0.10 mL (0.89 mmol) of methyl trifluoromethane sulfonate under argon. The clear mixture was stirred at ambient temperature for 30 min. A white precipitate was observed and the solution was stirred overnight. The white solid was collected by filtration and rinsed with dichloromethane, then dried under vacuum over P$_2$O$_5$ and refluxing water, 0.20 g, TLC (silica, 95:5 CH$_2$Cl$_2$) $R_f$ 0.56. $^1$H NMR (DMSO) 2.82 (t, J=6.9, 1H), 3.35 (dd, J=5.1, J=12, 1H), 4.14 (s, 3H), 4.73–4.82 (m, 1H), 4.88–4.96 (m, 2H), 6.89 (d, 1H), 7.21–7.44 (m, 10H), 8.52 (d, 2H). Anal. calcd. for C$_{22}$H$_{21}$N$_2$O$_2$+CF$_3$SO$_3$: C, 54.77; H, 4.39; N, 5.49; S, 6.28. Found: C, 56.51, 56.44; H, 4.96, 4.98; N, 5.50, 5.81; S, 6.64. The trifluoromethane sulfonate salt, 0.20 g was eluted from a 10 g Amberlite IRA-400 (Cl) resin column with methanol to afford 0.14 g of the chloride salt. TLC (silica, 95:5, CH$_2$Cl$_2$: CH$_3$OH) $R_f$ 0.10. Solids were recrystallized from hot ethanol and ether. Removal of solvent and drying of solids over P$_2$O$_5$/H$_2$O gave 0.110 g (32%) of a white solid. $^1$H NMR (CD$_3$OD) 2.82 (dd, J=10.8, J=13, 1H), 3.36 (dd, J=4.8, J=13, 1H), 4.15 (s, 3H), 4.74–4.81 (m, 1H), 4.92–5.0 (m, 2H), 6.89 (t, J=3, 1H), 7.21–7.45 (m, 10H), J-8.56 (d, 2H). IR (KBr) 3443, 3389, 3119, 3080, 1758, 1643, 1445, 1306, 1172, 1093, 971, 748, 704, 645 cm$^1$. Anal. calcd. for C$_{21}$H$_{21}$O$_2$N$_2$Cl+0.25 H$_2$O: C, 67.55; H, 5.80; N, 7.50; Cl, 9.50. Found: C, 67.27, 67.20; H, 5.81, 5.84; N, 7.44; Cl, 9.45. mp 216°–218.5° C.

Example 6

Methyl dihydro-5-[(4-methyl-1H-pyrazol-1-yl)methyl]-3,3-diphenyl-2(3H)-furanone chloride hydrate. To a solution of 0.537 g (1.59 mmol) of 4-methylpyrazole lactone in 5.0 mL of dichloromethane produced in accordance with Example 3 was added 0.18 mL (1.51 mmol) of methyl trifluoromethane sulfonate under argon. The mixture was stirred at ambient temperature for 40 h. The mixture was concentrated to an oily residue, TLC (silica, 95:5 CH$_2$Cl$_2$: CH$_3$OH) Rf 0.55. $^1$H NMR (DMSO) 2.09 (s, 3H), 2.82 (dd, J=10.8, J=13, 1H), 3.34 (dd, J=5.1, J=13, 1H), 3.77–3.79 (br s, H$_2$O), 4.09 (s, 3H), 4.67–4.80 (m, 1H), 4.83–4.90 (m, 2H), 7.23–7.44 (m, 10H), 8.33 (d, 2H). The trifluoromethane sulfonate salt, 0.81 g was eluted from a 45 g Amberlite IRA-400 (Cl) resin column with methanol. Filtration and removal of solvent afforded 0.56 g of a white solid. TLC (silica, 95:5, CH$_2$CL$_2$: CH$_3$OH) R$_f$ 0.14. mp 118°–121° C. $^1$H NMR (DMSO) 2.10 (s, 3H), 2.82 (dd, J=10.8, J=13, 1H), 3.34 (s, H$_2$O), 3.27 (dd, J=5, J=13, 1H), 4.12 (s, 3H), 4.68–4.78 (m, 1H), 4.92–4.96 (m, 2H), 7.22–7.41 (m, 10H), 8.40 (d, 2H). IR (KBr) 3397, 3114, 1759, 1499, 1455, 1409, 1365, 1167, 1067, 964, 756, 702 cm$^{-1}$. Removal of solvent and drying of solids over P$_2$O$_5$/H$_2$O gave 0.280 g (85%) of a white solid. Anal. calcd. for C$_{22}$H$_{23}$O$_2$N$_2$Cl+1.0H$_2$O: C, 65.91; H, 6.29; N, 6.99; Cl, 8.84. Found: C, 66.08, 65.99; H, 6.30, 6.33; N, 6.92, 6.91; Cl, 8.94.

Example 7

Methyl dihydro-5-[(3-methyl-1H-pyrazol-1-yl)methyl]-3,3-diphenyl-2(3H)-furanone chloride hydrate. To a solution of 0.280 g (0.84 mmol) of the 3-methylpyrazole lactone in 3.0 mL of dichloromethane produced according to Example 2 was added 0.10 mL (0.80 mmol) of methyl trifluoromethane sulfonate under argon. The mixture was stirred at ambient temperature for 48 h. The mixture was concentrated to 0.46 g of the crude trifluoromethane sulfonate salt. $^1$H NMR (DMSO) 2.45 (s, 3H), 2.80 (dd, J=10.8, J=13, 1H), 3.34 (dd, J=5.1, J=13, 1H), 3.9 (H$_2$O), 3.98 (s, 3H), 4.63–4.74 (m, 1H), 4.91–4.95 (m, 2H), 6.75 (d, 1H), 7.24–7.41 (m, 11H), 8.38 (d, 1H). The trifluoromethane sulfonate salt, 0.40 g was eluted on a 25 g Amberlite IRA-400 (Cl) resin column with methanol. Approximately 0.32 g of the chloride salt was obtained. TLC (silica, 95:5, CH$_2$Cl$_2$:CH$_3$OH) R$_f$ 0.10. SOlids were recrystallized from hot ethanol then dissolved and filtered with 50:50 dichloromethane:ethanol to remove particulate matter. $^1$H NMR (DMSO) 2.45 (s, 3H), 2.82 (dd, J=10.8, J=13, 1H), 3.15 (H$_2$O), 3.26 (dd, J=5.1, J=13, 1H), 3.98 (s, 3H), 4.65–4.75 (m, 1H), 4.90–4.95 (m, 2H), 6.75 (d, 1H), 7.21–7.41 (m, 10H). IR (KBr) 3499, 3124, 2944, 1761, 1540, 1496, 1398, 1234, 1175, 1162, 1069, 1054, 965, 745, 697 cm$^{-1}$. Removal of solvent and drying of solids over P$_2$O$_5$/H$_2$O gave 0.280 g (85%) of a white solid. Anal. calcd. for C$_{22}$H$_{23}$O$_2$N$_2$Cl+0.5 H$_2$O: C, 67.43; H, 6.17; N, 7.15; Cl, 9.05. Found: C, 67.30; H, 6.23; N, 7.07; Cl, 9.03 mp 214°–216° C.

Example 8

Ethyl dihydro-3,3-diphenyl-5-(1H-pyrazol-1-ylmethyl)-2(3H)-furanone chloride. To a solution of 1.10 g (3.45 mmol) of dihydro-3,3-diphenyl-5-(1H-pyrazol-1-ylmethyl)-2(3H)-furanone in 8.0 mL of dichloromethane produced in accordance with Example 1 was added 0.50 mL (3.80 mmol) of ethyl trifluoromethanesulfonate. The solution was stirred at ambient temperature for 70 h; then the solution was concentrated to a crude solid. Solids were dissolved in dichloromethane, then poured into water (checked pH=2). The dichloromethane layer was washed with saturated sodium carbonate (2×200 mL), water (2×200 mL), and dried over Na$_2$SO$_4$. Filtration and removal of solvent gave a tan solid which was recrystallized from a minimal volume of hot ethanol. The triflate salts were dried to afford 0.56 g (33%) of a solid. TLC (silica, 95:5, CH$_2$Cl$_2$: CH$_3$OH) R$_f$ 0.28, 0.10. Chromatography on 52 g of Merck silica gel (230–400 mesh) eluted with dichloromethane: methanol (95:5) afforded an oil, TLC (silica, CH$_2$Cl$_2$:CH$_3$OH 95:5) R$_f$ 0.12. Crystallization from ethanol afforded 0.45 g (27%) of a white solid, mp 145°–147.5° C. $^1$H NMR (DMSO) 1.45 (t, J=6.9, 3H), 2.84 (dd, J=10.5, J=13, 1H), 3.25 (s, D$_2$O), 3.29 (s, H$_2$O), 3.36 (dd, J=5.1, J=13, 1H), 4.56 (ABq, J=7.2,Δυ=12, 1H), 4.7–4.78 (m, 1H), 4.9–5.01 (m, 2H), 6.95 (t, J=2.7, 1H), 7.25–7.41 (m, 10H), 8.56 (d, 1H), 8.62 (d, 1H). Anal. calcd. for C$_{22}$H$_{23}$N$_2$O$_2$+CF$_3$SO$_4$: C, 55.64; H, 4.67; N, 5.64; S, 6.46. Found: C, 55.49; H, 4.68; N, 5.61; S, 6.56. Exchange of 0.32 g of the trifluoromethanesolfonate anion for chloride was made by methanol elution of the solid materials from a prepared Amberlite 400 (Cl) exchange resin (110 g). The obtained oil was dissolved in hot ethanol and diluted with a small volume of ether. The crystals were collected by filtration and dried to afford 0.190 g (80%) of a white solid, mp 239°–241° C. $^1$H NMR (CD$_3$OD) 1.58 (t, J=72, 3H, CH$_3$), 2.82 (dd, J=10.2, J=13, 1H, CH$_2$), 3.37 (dd, J=5.1, J=13, 1H, CH$_2$), 4.59 (ABq, J=7.2,Δυ=14.7, 2H, CH$_2$), 4.76–4.82 (m, 1H, CH), 4 86–5.10 (m, 2H, CH$_2$), 6.90 (t, J=3.0, 1H), 7.28–7.40 (m, 10H, C$_6$H$_5$), 8.45 (d, 1H, CH), 8.49 (d, 1H, CH). IR (KBr) 3137, 3062, 2954, 1759, 1497, 1463, 1435, 1296, 1241, 1167, 1090, 969. Anal. calcd. for C$_{22}$H$_{23}$N$_2$O$_2$Cl: C, 69.01; H, 6.05; N, 7.31; Cl, 9.26. Found: C,55.64; H, 4.67; N, 5.64; S, Found C, 68.90; H, 6.07; N, 7.25; Cl, 9.17.

Example 9

Ethyl dihydro-5-[(3-methyl-1H-pyrazol-1-yl)methyl]-3,3-diphenyl-2(3H)-furanone chloride hydrate. To a solution of 0.77 g (2.3 mmol) of the 3-methylpyrazole lactone in 5.0 mL of dichloromethane produced in accordance with Example 2 was added dropwise 0.40 mL (3.0 mmol) of ethyl trifluoromethane sulfonate under argon. The mixture was stirred at ambient temperature over the weekend. The mixture was concentrated to a residue, 0.7 g TLC (silica, 95:5 CH$_2$Cl$_2$) R$_f$ 0.66; 0.37 (major product) Flash chromatography on merck silica gel with dichloromethane/methanol (95:5) gave 0.55 g of the trifluoromethanesulfonate salt which was recrystallized from hot ethanol to afford 0.310 g of the salt. $^1$H NMR (DMSO) 1.27 (t, J=6.9, BH), 2.40 (dd, J=10.8, J=13, 1H), 3.24 (dd, J=5.1, J=13, 1H), 3.2–3.35 (m), 4.45–4.55 (m 2H), 4.60–4.69 (m, 1H), 4.80–4.98 (m, 2H), 6.77 (d, 1H), 7.23–7.41 (m, 11H), 8.43 (d, 1H). Anal.

calcd. for $C_{23}H_{25}N_2O_2+CF_3SO_3$: C, 56.46; H, 4.94; N, 5.49; S, 6.28). Found: C, 56.51, 56.44; H, 4.96, 4.98; N, 5.50, 5.43; S, 6.36. The trifluoromethane sulfonate salt, 0.20 g was eluted on a 29 g Amberlite IRA-400 (Cl) resin column with methanol to afford 0 18 g of the chloride salt. TLC (silica, 95:5, $CH_2CL_2$:$CH_3OH$) $R_f$ 0.10. Solids were recrystallized from hot ethanol and ether. Removal of solvent and drying of solids over $P_2O_5/H_2O$ gave 0.150 g (20%) of a white solid. $^1H$ NMR ($CD_3OD$) 1.40 (t, J=7, 3H), 2.55 (s, 3H), 2.82 (dd, J=10.8, J=13, 1H), 3.36 (dd, J=5.1, J=13, 1H), 4.60 (ABq, 2H), 4.80 ($H_2O$), 4.65–4.94 (m, 3H), 6.73 (d, 1H), 7.25–7.34 (m, 10H), 8.33 (d, 1H). IR (KBr) 3494, 3424, 3103, 3062, 2990, 2944, 1766, 1537, 1476, 1448, 1162, 964, 750, 704 cm$^1$. Anal. calcd. for $C_{22}H_{23}O_2N_2Cl+1.0$ $H_2O$: C, 66.58; H, 6.56; N, 6.75; Cl, 8.54. Found: C, 66.63, 66.53; H, 6.57, 6.58; N, 6.77; Cl, 8.60 mp 213°–215.5° C.

Example 10

Ethyl dihydro-5-[(4-methyl-1H-pyrazol-1-yl)methyl]-3,3-diphenyl-2(3H)-furanone chloride hydrate. To a solution of 1.00 g (3.00 mmol of 4-methylpyrazole lactone in 3.0 mL of dichloromethane Produced in accordance with Example 3 was added 0.43 mL (3.31 mmol) of ethyl trifluoromethanesulfonate. The solution was stirred at ambient temperature for 48 h, then the solution was concentrated to a dark oil, about 2 g. Chromatography on 80 g of Merck silica gel (230–400 mesh) eluted with dichloromethane:methanol (92:8) afforded an oil, TLC (silica, $CH_2Cl_2$:$CH_3OH$ 90:10) $R_f$ 0.52. Crystallization from 2-propanol afforded 0.83 g (55%) of a white solid, mp 135.5°–137.5° C. $^1H$ NMR (DMSO) 1.43 (t, J=7.2, 3H), 2.10 (s, 3H), 2.84 (dd, J=10.5, J=13, 1H), 3.30 (s, $D_2O$), 3.32 (s, $H_2O$), 3.34 (dd, J=5.1, J=13, 1H), 4.48 (ABq, J=7.2,$\Delta v$=14.4, 1H), 4.65–4.76 (m, 1H), 4.5–4.99 (m, 2H), 7.25–7.5 (M, 10H), 8.37 (s, 1H). Anal. calcd. for $C_{23}H_{25}N_2O_2 +CF_3SO_3$: C, 56.46; H, 4.94; N, 5.49; S, 6.28. Found: C, 56.53; H, 4.97; N, 5.49; S, 6.18. Exchange of the trifluoromethanesulfonate anion for chloride was made by methanol elution of the solid materials from a prepared Amberlite 400 (Cl) exchange resin (110 g). The obtained oil was dissolved in hot ethanol and diluted with a small volume of ether. The crystals were collected by filtration and dried to afford 0.440 g (37%) of a white solid, mp 240.5°–242° C. $^1H$ NMR ($CD_3OD$) 1.55 (t, J=7.2, 3H, $CH_3$), 2.19 (s, 3H, $CH_3$), 2.82 (dd, J=10.2, J=13, 1H, $CH_2$), 3.36 (dd, J=5.1, J=13, 1H, $CH_2$), 4.52 (AB$_g$, J=7.2,$\Delta v$=14.7, 2H, $CH_2$), 4.7–4.8 (m, 1H, CH), 4.82–4.97 (m, 2H, $CH_2$), 7.25–7.40 (m, 10H, $C_6H_5$), 8.24 (s, 1H, CH), 8.29 (s, 1H, CH). IR (KBr) 3386, 3106, 3062, 3021, 2975, 1759, 1499, 1448, 1363, 1167, 1064, 967 cm$^{-1}$. Anal. calcd. for $C_{23}H_{25}N_2O_2Cl+0.75$ $H_2O$: C, 67.31; H, 6.51; N, 6.83; Cl, 8.64. Found: C, 67.33, 67.25; H, 6.48, 6.52; N, 6.84; Cl, 8.56.

Example 11

Antimuscarinic Test Protocol. This protocol was designed to identify compounds that possess antagonist activity at postsynaptic muscarinic cholinergic receptors on intestinal (ileal-longitudinal) smooth muscle and bladder detrusor muscle.

Preparation of Ileum for Testing

Male albino guinea pigs are killed by decapitation or cervical dislocation. The cavity is opened and the small intestine is removed, with about 10 cm of the terminal ileum being discarded. The intestine is placed in a Petri dish that contains Tyrodes solution (137 mM NaCl, 2.78 mM KCl, 1.8 mM $CaCl_2.2H_2O$, 1.1 mM $MgCl_2.6H_2O$, 0.4 mM $NaH_3PO_4$, 11.8 mM $NaHCO_3$, 5.6 mM dextrose) and cut into 3–4 cm segments. The segments are preferentially taken from the aboral end of the ileum. Each segment is carefully stretched onto a glass rod 6 mm in diameter and the remaining mesenteric tissue is cut away. The longitudinal muscle, with the myenteric plexus attached, is separated from the underlying circular muscle by gently stroking with a cotton-tipped applicator soaked in Tyrodes solution on a tangent away from the shallow longitudinal incisions made parallel to the mesenteric attachment. Using gentle traction, and taking care to keep the segment moist throughout the whole procedure, the tissue is stripped from the whole length of the segment (Paton and Zar, *J. Physiol.* 194:13, 1968).

Tissues are suspended with 5-0 silk suture in 10 mL water-jacketed glass tissue baths containing Tyrodes solution maintained at 37° C. and aerated with 95% $O_2$/5% $CO_2$. The suture connects each tissue to an isometric force-displacement transducer (Grass or Gould) coupled to a physiograph. Each preparation is suspended under a resting tension of 0.3 g and allowed to equilibrate for 36 minutes. During this period, the baths are emptied and filled every 12 minutes with 10 mL of warm Tyrodes solution. At the end of this equilibration period, each muscle strip is conditioned by adding 10 mM carbachol to the baths. The drug remains in contact with each tissue for 1–2 minutes and then is removed from the bath with 4 rapid rinses of 10 mL of warm Tyrodes solution. The preparations are allowed to recover for an additional 12 minutes before being used in experiments.

Preparation of Agonist

Carbachol is dissolved in saline to produce $2\times10^{-2}$M stock concentrations. Serial dilutions (1:10) in saline or water are made from the stock solution. Appropriate volumes of these solutions are added cumulatively to the 10 mL tissue baths in order to obtain the desired bath concentrations.

Preparation of Test Compounds

Compounds that are soluble in water or saline are dissolved in these solvents to produce $2\times10^{-2}$ or $2\times10^{-3}$M stock concentrations. Small amounts of 1 N HCl, NaOH, or 95ethanol may be added for those agents that are not soluble in water or saline alone. Serial dilutions (1:10) in aqueous solvents are dissolved in dimethylsulfoxide (DMSO) to produce $4\times10^{-2}$M stock solutions. Serial dilutions (1:10) in water are made from the stock solution. Other solvents may be used when appropriate and will be specifically described in the experimental procedure. Appropriate volumes are then added to the baths in order to obtain the desired bath concentrations.

Experimental Procedure

Appropriate volumes of carbachol solutions are cumulatively added to the 10 mL tissue baths to increase the concentration of carbachol in the bath step-by-step without washing out after each single dose. With each concentration step, the tissue contracts isometrically. The next concentration is added only after the preceding contraction has reached a steady value. When the next concentration step does not cause a further decrease in contraction, it is assumed that the maximum effect has been obtained. The tissue is then washed with 4 rapid rinses of 10 mL of warm Tyrodes solution and allowed to recover for 12 minutes [Van Rossum et al., *Arch. Int. Pharmacodyn.* 143:240, (1963) and 143:299, (1963)]. Antagonism of carbachol responses in the presence of antagonist is determined by repeating the cumulative addition procedure after the tissue has been exposed to the agonist for 5 minutes.

Three or four different concentrations of antagonist are studied in the same preparations. Responses are expressed relative to the maximum contraction elicited by carbachol in the absence of antagonist. The data are collected via Buxco Data Logger and analyzed by Branch Technology's software Package to obtain $K_b$ values for the antagonists.

TABLE 1

| Test Compound | Anti-muscarinic Activity $K_b$ (nM) (ileum strips) |
|---|---|
| Atropine | 1.7 |
| dihydro-3,3-diphenyl-5-(1H-pyrazol-1-ylmethyl)-2(3H)-furanone | 50 |
| dihydro-5-[(3-methyl-1H-pyrazol-1-yl)methyl]-3,3-diphenyl-2(3H)-furanone | 239 |
| dihydro-5-[(4-methyl-1H-pyrazol-1-yl)methyl]-3,3-diphenyl-2(3H)-furanone | 251 |
| dihydro-5-[(3,5-dimethyl-1H-pyrazol-1-yl)methyl]-3,3-diphenyl-2(3H)-furanone hydrochloride | 1000 |
| methyl dihydro-3,3-diphenyl-5-(1H-pyrazol-1-ylmethyl)-2(3H)-furanone chloride hydrate | 100 |
| methyl dihydro-5-[(3-methyl-1H-pyrazol-1-yl)methyl]-3,3-diphenyl-2(3H)-furanone chloride hydrate | 142 |
| methyl dihydro-5-[(4-methyl-1H-pyrazol-1-yl)methyl]-3,3-diphenyl-2(3H)-furanone chloride hydrate | 117 |
| ethyl dihydro-3,3-diphenyl-5-(1H-pyrazol-1-yl)methyl]-2(3H)-furanone chloride | 49 |
| ethyl dihydro-5-[(3-methyl-1H-pyrazol-1-yl)methyl]-3,3-diphenyl-2(3H)-furanone chloride hydrate | 52 |
| ethyl dihydro-5-[(4-methyl-1H-pyrazol-1-yl)methyl]-3,3-diphenyl-2(3H)-furanone chloride hydrate | 148 |

What is claimed is:

1. A compound of the formula:

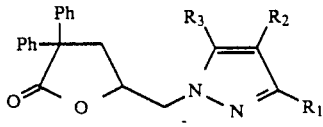

wherein:
$R_1$ is hydrogen or lower alkyl,
$R_2$ is hydrogen or lower alkyl,
$R_3$ is hydrogen or lower alkyl, and
Ph is phenyl
and the pharmaceutically acceptable lower alkyl quaternary and acid addition salts thereof.

2. The compound of claim 1 which is dihydro-3,3-diphenyl-5-(1H-pyrazol-1-ylmethyl)-2(3H)-furanome.

3. The compound of claim 1 which is dihydro-5-[(3-methyl-1H-pyrazol-1-yl)methyl]-3,3-diphenyl-2(3H)-furanone.

4. The compound of claim 1 which is dihydro-5-[(4-methyl-1H-pyrazol-1-yl)methyl]-3,3 diphenyl-2(3H)-furanone.

5. The compound of claim 1 which is dihydro-5-[(5-methyl-1H-pyrazol-1-yl)methyl]-3,3-diphenyl-2(3H)-furanone.

6. The compound of claim 1 which is dihydro-5-[(3,5-dimethyl-1H-pyrazol-1-yl)methyl]-3,3-diphenyl-2(3H)-furanone hydrochloride.

7. The compound of claim 1 which is dihydro-5-[(3,4-dimethyl-1H-pyrazol-1-yl)methyl]-3,3-diphenyl-2(3H)-furanone hydrochloride.

8. The compound of claim 1 which is dihydro-5-[(4,5-dimethyl-1H-pyrazol-1-yl)methyl]-3,3-diphenyl-2(3H)-furanone hydrochloride.

9. The compound of claim 1 which is methyl dihydro-3,3-diphenyl-5-(1H-pyrazol-1-ylmethyl)-2(3H)-furanone chloride.

10. The compound of claim 1 which is ethyl dihydro-3,3-diphenyl-5-(1H-pyrazol-1-ylmethyl)-2(3H) -furanone chloride.

11. The compound of claim 1 which is methyl dihydro-5-[(3-methyl-1H-pyrazol-1-yl)methyl]-3,3-diphenyl-2(3H)-furanone chloride.

12. The compound of claim 1 which is ethyl dihydro-5-[(3-methyl-1H-pyrazol-1-yl)methyl]-3,3-diphenyl-2(3H)-furanone chloride.

13. The compound of claim 1 which is methyl dihydro-5-[(4-methyl-1H-pyrazol-1-yl)methyl]-3,3-diphenyl-2(3H)-furanone chloride.

14. The compound of claim 1 which is ethyl dihydro-5-[(4-methyl-1H-pyrazol-1-yl)methyl]-3,3-diphenyl-2(3H)-furanone chloride.

15. The compound of claim 1 which is methyl dihydro-5-[(5-methyl-1H-pyrazol-1-yl)methyl]-3,3-diphenyl 2(3H)-furanone chloride.

16. The compound of claim 1 which is ethyl dihydro-5-[(5-methyl-1H-pyrazol-1-yl)methyl]-3,3-diphenyl-2(3H)-furanone chloride.

17. The compound of claim 1 which is methyl dihydro-5-[(3,5-dimethyl-1H-pyrazol-1-yl)methyl]-3,3-diphenyl-2(3H)-furanone chloride.

18. The compound of claim 1 which is ethyl dihydro-5-[(3,5-dimethyl-1H-pyrazol-1-yl)methyl]-3,3-diphenyl-2(3H)-furanone chloride.

19. The compound of claim 1 which is methyl dihydro-5-[(3,4-dimethyl-1H-pyrazol-1-yl)methyl]-3,3-diphenyl-2(3H)-furanone chloride.

20. The compound of claim 1 which is ethyl dihydro-5-[(3,4-dimethyl-1H-pyrazol-1-yl)methyl]-3,3-diphenyl-2(3H)-furanone chloride.

21. The compound of claim 1 which is methyl dihydro-5-[(4,5-dimethyl-1H-pyrazol-1-yl)methyl]-3,3-diphenyl-2(3H)-furanone chloride.

22. The compound of claim 1 which is ethyl dihydro-5-[(4,5-dimethyl-1H-pyrazol-1-yl)methyl]-3,3-diphenyl-2(3H)-furanone chloride.

23. A method of promoting anticholinergic activity in a patient comprising administering to the patient an effective amount of a compound having the formula:

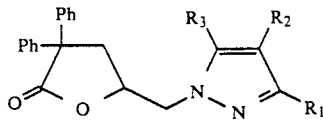

wherein:
$R_1$ is hydrogen or lower alkyl,
$R_2$ is hydrogen or lower alkyl,
$R_3$ is hydrogen or lower alkyl, and Ph is phenyl and the pharmaceutically acceptable lower alkyl quaternary and acid addition salts thereof.

24. A pharmaceutical composition comprising (i) a compound of the formula

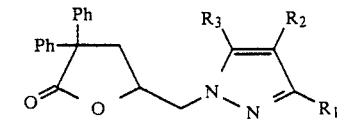

wherein:
R$_1$ is hydrogen or lower alkyl,
R$_2$ is hydrogen or lower alkyl,
R$_3$ is hydrogen or lower alkyl, and
Ph is phenyl
or a pharmaceutically acceptable salt thereof and (ii) a pharmaceutically acceptable carrier.

* * * * *